(12) United States Patent
Vo-Dinh (10) Patent No.: US 7,951,535 B2
(45) Date of Patent: May 31, 2011

(54) SERS MOLECULAR PROBE FOR DIAGNOSTICS AND THERAPY AND METHODS OF USE THEREOF

(75) Inventor: Tuan Vo-Dinh, Knoxville, TN (US)

(73) Assignee: U-T Battelle, LLC, Oak Ridge, TN (US)

( * ) Notice: Subject to any disclaimer, the term of this patent is extended or adjusted under 35 U.S.C. 154(b) by 496 days.

(21) Appl. No.: 11/972,110

(22) Filed: Jan. 10, 2008

(65) Prior Publication Data

US 2008/0219926 A1    Sep. 11, 2008

Related U.S. Application Data

(62) Division of application No. 10/677,690, filed on Oct. 2, 2003, now abandoned.

(51) Int. Cl.
*C12Q 1/68* (2006.01)
*G01J 3/44* (2006.01)
*C07H 21/02* (2006.01)
*C07H 21/04* (2006.01)

(52) U.S. Cl. ............ 435/6; 356/301; 536/23.1; 536/24.3

(58) Field of Classification Search .................. None
See application file for complete search history.

(56) References Cited

U.S. PATENT DOCUMENTS

| 6,117,635 | A | 9/2000 | Nazarenko et al. |
| 6,417,340 | B1 | 7/2002 | Mirkin et al. |
| 7,267,948 | B2 | 9/2007 | Vo-Dinh |

FOREIGN PATENT DOCUMENTS

WO    WO 02/18951    3/2002

OTHER PUBLICATIONS

Vo-Dinh, T. et al., J. Raman Spectrosc., vol. 33, pp. 511-516 (Jul. 2002).*
Wabuyele, M. B. et al., Anal. Chem., vol. 77, pp. 7810-7815 (2005).*
Wabuyele, M.B. et al., Rev. Sci. Intrum., vol. 76, 063710, p. 1-7 (2005).*
Chithrani, B. D. et al., Nano Letters, vol. 6, pp. 662-668 (2006).*
Scaffidi, J. P. et al., Anal. Bioanal. Chem., vol. 393, p. 1135-1141 (2009).*
Tyagi, S., et al., "Molecular Beacons: Probes That Fluoresce Upon Hybridization", Bio/Technology, vol. 14, Issue 3, (Mar. 1996).

(Continued)

*Primary Examiner* — Teresa E Strzelecka
(74) *Attorney, Agent, or Firm* — Novak Druce + Quigg LLP; Gregory A. Nelson; Amy A. Dobbelaere (57) ABSTRACT

An oligonucleotide-based SERS molecular probe (SMP) includes a nanoparticle having at least a metal component, and at least one pin loop, the pin loop including a loop sequence complementary to at least one target sequence, a first stem attached to one end of the loop sequence, a second stem attached to the other end of the loop sequence, and at least one SERS active label attached to the first stem. The nanoparticle is attached to the second stem. The probe generates a stronger SERS signal upon irradiation with excitation radiation when not bound to the target sequence as compared to the SERS signal generated following hybridization of the probe with the target sequence.

6 Claims, 7 Drawing Sheets

OTHER PUBLICATIONS

Kneipp, K., et al., "Single Molecule Detection Using Surface-Enhanced Raman Scattering", Phys. Rev. Letters 78, p. 1667, (1997).

Nie, S., et al., "Proving Single Molecules and Single Nanoparticles by Surface-Enhanced Raman Scattering", Science, vol. 275, No. 5303, pp. 1102-1106 (Feb. 21, 1997).

Schofield, P., et al., "Molecular Beacons: Trial of a Fluorescence-based Solution Hybridization Technique for Ecological Studies with Ruminal Bacteria", Applied and Environmental Microbiology, vol. 63, No. 3, pp. 1143-1147, (Mar. 1997).

Sershen, S.R., et al., "Temperature-sensitive Polymer-nanoshell Composites for Photothermally Modulated Drug Delivery", J. Biomed. Mat. Res., vol. 51, No. 3, pp. 293-298, 2000.

Deng, W., et al., "Silver Ions Adsorbed to Self-assembled Monolayers of Alkanedithiols on Gold Surfaces Form Ag-Dithiol-Au Multilayer Structures", Applied Physics, vol. 71, pp. 639-642, (2000).

Behlke, M., "Fluorescence Resonance Energy Transfer", Integrated DNA Technologies, Technical Bulletin, (Dec. 2000).

Devor, E., et al., "Molecular Beacons", Integrated DNA Technologies, Technical Bulletin, (May 2000).

Schulte et al., Biomedical Imaging: Macro to Nano, IEEE Int'l Symposium, pp. 1354-1356, Apr. 15-18, 1984.

Lakowicz, Principles of Fluorescence Spectroscopy, 2d ed., Kluwer Academic/Plenum Publishers, pp. 25-61, 1999.

* cited by examiner

SERS MOLECULAR PROBE FOR DIAGNOSTICS AND THERAPY AND METHODS OF USE THEREOF

CROSS-REFERENCE TO RELATED APPLICATIONS

This application is a divisional application of U.S. application Ser. No. 10/677,690, filed Oct. 2, 3003, abandoned May 23, 2008, which is incorporated herein by reference.

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

The invention relates to Surface Enhanced Raman Spectroscopy (SERS) based molecular probes and use of the same for diagnostics and therapy.

BACKGROUND OF THE INVENTION

There is a demand for a sensitive and selective method for in vitro and in vivo medical diagnostics and treatment of disease at the molecular level. In addition, there is a demand for a rapid, simple, cost-effective technique for screening air, water and biological samples, such as blood, saliva, bodily fluid, cells, tissues and organs to identify various components therein. Screening can involve detection of biochemical and biological species such as harmful chemicals, bacteria, viruses, defected genes, proteins, metabolites and biomarkers of diseases in organs, tissues and cells. Furthermore, there is a need for early detection of biological and chemical warfare agents for homeland defense.

Screening can also be used to identify the presence or absence of medical diseases and infectious pathogens. Regarding biological fluids, tissues, and organs, the use of inexpensive screening analyses can allow the rapid detection and improved treatments of many illnesses. Rapid and effective medical screening tests can also reduce the cost of health care by preventing unnecessary and generally more costly reactive medical treatments.

A critical factor in many diagnostics is the rapid, selective, and sensitive detection of biochemical substances, such as proteins, metabolites, nucleic acids, biological species or living systems, such as bacteria, virus or related components at ultra-trace levels in samples, tissues or organs of interest. In the case of medical diagnostic applications, biological samples can include tissues, blood and other bodily fluids. To achieve the required level of sensitivity and specificity in detection, it is often necessary to use a method that is capable of identifying and differentiating between a large number of biochemical constituents in complex mixed samples.

Living systems possess exquisite recognition elements often called bioreceptors, such as antibodies, proteins, enzymes and genes, which allow specific identification and detection of complex chemical and biological species. Molecular probes, which comprise a bioreceptor for molecular recognition and binding and a label for detection, exploit this powerful molecular recognition capability of bioreceptors. Due to the high level of specificity of the DNA hybridization process, there is an increasing interest in the development of DNA bioreceptor-based molecular probe systems. Applications for these systems include infectious disease identification, medical diagnostics and therapy, biotechnology and environmental bioremediation.

Nucleic acid based molecular probe systems can be designed using simple rules to recognize and detect a wide variety of targets with almost any desired degree of specificity. Moreover, such probe-based systems can be chemically produced with relative ease. Synthetic oligonucleotides can be made specific for desired sequences by varying length, sequence, and hybridization conditions of the probe oligonucleotide to permit identification and quantification of the presence of its complementary sequence within a heterogeneous mixture.

Peptide Nucleic Acid (PNA) is a system similar to DNA in which the backbone is a pseudopeptide rather than a sugar. PNA functions in a manner similar to DNA and binds to complementary nucleic acid strands. The neutral backbone of PNA often leads to stronger binding and greater specificity than normally achieved with DNA. In addition, the unique chemical, physical and biological properties of PNA have been exploited to produce powerful molecular probes. Important new applications have emerged that could not be performed using oligonucleotides.

There has been recent research and development relating to molecular probes and related detection systems called biosensors. One type of biosensor device, often referred to as a "biochip," applies spectroscopy using a semiconductor-based detection system and biotechnology-based probes. These probes have generally included luminescence labels, such as fluorescent or chemiluminescent labels for gene detection. Although sensitivities achieved by luminescence techniques are generally adequate for certain applications, alternative techniques with improved spectral selectivities are desirable to overcome the limited spectral specificity generally provided by luminescent labels.

Spectroscopy involves an analytical detection technique concerned with the measurement of the interaction of radiant energy with matter and with the interpretation of the interaction both at the fundamental level and for practical analysis. Interpretation of the spectra produced by various spectroscopic instrumentation has been used to provide fundamental information on the atomic and molecular energy levels, the distribution of species within those levels, the nature of processes involving change from one level to another, molecular geometries, chemical bonding, and interaction of molecules in solution. Comparisons of spectra have provided a basis for the determination of qualitative chemical composition and chemical structure, and for quantitative chemical analysis.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure. If the vibrational spectrum is to be measured by an optical absorption process, optical fibers deliver light from a light source to a sample, and after passage of the light through the sample, the optical signal generated by the exciting optical energy is collected. This collected light is directed to a monochromator equipped with a photodetector for analyzing its wavelength and/or intensity.

One particular spectroscopic technique, known as Raman spectroscopy, utilizes the Raman effect, which is a phenomenon observed in the scattering of light as it is reflected by a material medium, whereby the light experiences a change in frequency and a random alteration in phase. When light is scattered from a molecule, most photons are elastically scattered. The scattered photons have the same energy (frequency) and, therefore, wavelength, as the incident photons. However, a small fraction of light (approximately 1 in $10^7$ photons) is scattered at optical frequencies different from, and usually lower than, the frequency of the incident photons. The process leading to this inelastic scatter is termed the Raman effect. Raman scattering can occur with a change in vibrational, rotational or electronic energy of a molecule.

The difference in energy between the incident photon and the Raman scattered photon is equal to the energy of a vibration of the scattering molecule. A plot of intensity of scattered light versus energy difference is a Raman spectrum. The wavelengths present in the scattered optical energy are characteristic of the structure of the molecule, and the intensity of this optical energy is dependent on the concentration of these molecules.

Numerically, the energy difference between the initial and final vibrational levels, v, or Raman shift in wavenumbers ($cm^{-1}$), is calculated through equation 1 below:

$$v=(1/\lambda_{incident})-(1/\lambda_{scattered}) \quad (1)$$

Where $\lambda_{incident}$ and $\lambda_{scattered}$ are wavelengths (in cm) of the incident and Raman scattered photons, respectively. The vibrational energy is ultimately dissipated as heat. Because of the low intensity of Raman scattering, heat dissipation does not cause a measurable temperature rise in the material.

Raman spectroscopy is complementary to fluorescence, and has been used as an analytical tool for certain applications due to its excellent specificity for chemical group identification. However, low sensitivity historically has limited its applications. Recently, the Raman technique has been rejuvenated following the discovery of a Raman enhancement of up to $10^6$ to $10^{10}$ for molecules adsorbed on microstructures of metal surfaces. The technique associated with this phenomenon is known as surface-enhanced Raman scattering (SERS) spectroscopy. The enhancement is due to a microstructured metal surface scattering process which increases the intrinsically weak normal Raman scattering (NRS) due to a combination of several electromagnetic and chemical effects between the molecule adsorbed on the metal surface and the metal surface itself.

The enhancement is primarily due to plasmon excitation at the metal surface. Thus, the effect is generally limited to Cu, Ag and Au, and to a few other metals for which surface plasmons are excited by visible radiation. Although chemisorption is not essential, when it does occur there may be further enhancement of the Raman signal, since the formation of new chemical bonds and the consequent perturbation of adsorbate electronic energy levels can lead to a surface-induced resonance effect. The combination of surface- and resonance-enhancement, often referred to as surface-enhanced resonance Raman scattering (SERRS) can occur when adsorbates have intense electronic absorption bands in the same spectral region as the metal surface plasmon resonance, yielding an overall enhancement as large as $10^{10}$ to $10^{12}$.

Nanoparticles can comprise solid metal of nanoscale size or nanoparticles coated with metal layers. Nanospheres of dielectric materials coated with a thin layer of silver (metal nanoshell) have been found to be SERS active. Nanospheres of magnetic materials coated with a thin layer of metal can also be used as SERS-active magnetic nanoparticles. The core diameter and the metal thickness of nanoshells can be varied to modify the SERS properties of the nanoparticles as disclosed in an article co-authored by the inventor. [R. L. Moody, T. Vo-Dinh, and W. H. Fletcher, "Investigation of Experimental Parameters for Surface-Enhanced Raman Spectroscopy," Appl. Spectrosc., 41, 966 (1987)].

A useful non-Raman based assaying techniques using stem-loop oligonucleotide probes has been disclosed. These probes are referred to as "molecular beacons" and were first disclosed as providing a rapid, quantitative assay technique by Tyagi and Kramer (Tyagi, S., F. R. Nature Biotechnology, 14, 303-308 (1996)). Molecular beacons are designed to have loop sequences which are complementary to a target nucleic acid (e.g., rRNA). The loop sequence is disposed between a first and a second stem sequence, the respective stem sequences being complements of one another. The molecular beacon includes a fluorescent molecule on the end of the first stem and a quenching molecule on the end of the second stem.

In the absence of the complementary target sequence the fluorescence upon irradiation remains low (quenched) due to physical proximity between the fluorophore and the quencher. When the complementary sequence is present, the loop opens and the fluorophore and the quencher separate so that they are no longer in physical proximity, so that the molecular probe generates relatively strong fluorescent signal upon irradiation when target nucleic acids are present.

SUMMARY OF THE INVENTION

An oligonucleotide-based SERS molecular probe (SMP) includes a nanoparticle having at least a metal component, and at least one pin loop, the pin loop including a loop sequence complementary to at least one target sequence, a first stem attached to one end of the loop sequence, a second stem attached to the other end of the loop sequence, and at least one SERS active label attached to the first stem. The nanoparticle is attached to the second stem. The probe generates a stronger SERS signal upon irradiation with excitation radiation when not bound to the target sequence as compared to a SERS signal following hybridization of the probe with said target sequence. The loop sequence can include DNA or PNA segments. The first and second stems are preferably complementary sequences.

The nanoparticle can be entirely a metal nanoparticle, or a combination of metal and non-metal components. For example, in the case of the combination metal and non-metal components, the nanoparticle can comprise an electrically insulating core coated with a metallic surface. Alternatively, the nanoparticle can comprise a metallic core coated with a thin (e.g. several Angstroms to nanometers thick) non-metal coating, such as silica, a polymer, protein, antibody or other bioreceptor. The combination metal and non-metal nanoparticles can have continuous or non-continuous coating layers.

The at least one pin loop can comprise a plurality of pin loops bound to the nanoparticle, the plurality of pin loops providing at least two different loop sequences having different labels for simultaneously detecting a plurality of target sequences. Each loop sequences can be targeted to a different DNA target sequence. This "multiplex" SERS molecular probe allows diagnostics of multiple targets simultaneously.

In a related multiplex arrangement, the SMP can be part of an interconnected SMP network, comprising a plurality of nanoparticles bound to one another. Each nanoparticle can support a very large number of SMPs, which can all be different, such as 100 or more. The nanoparticles can be bound to one another by DNA strands or thiol chemistry.

The at least one SERS active label can comprise at least a first and second SERS label, said first and second SERS label providing different emission characteristics. By using a combination of multiple labels, otherwise identical SMP probes can be distinguished from one another thus extending the number of distinguishable SMP types.

The SMP can include a bioreceptor attached thereto. Bioreceptors can include an antibody, a protein, a biomimetic, an enzyme, a gene, a cell receptor and an intact biological cell. The bioreceptor adds functionality to SMP and allows it to be targeted to specific biotargets. For example, an antibody targeted against specific cancer cells to allow targeting the SMP to these specific biotargets. This provides a "dual-functionality" to the SMP probe. In this arrangement, the bioreceptor is for targeting and label together with the nanoparticle is for diagnostics/detection.

A Raman detection system can comprise at least one excitation light source for providing excitation radiation and at least one SMP as described above. The system can include a detection system communicably connected to the SMP for detection of SERS signals emanating from the SMP. The at least one SMP can comprise a plurality of SMPs, the plurality of SMPs bound to a solid sampling platform. The detection system can include a photomultiplier, a charge-coupled device (CCD), a charge injection device (CID), photodiode, phototransistor or avalanche diode. The detection system can be integrated circuit based.

When the at least one SMP comprises a plurality of SMPs, the detection system can provide a separate photodetector channel for receipt of SERS signals emanated from each of the plurality of SMPs. In this embodiment, the separate photodetector channels preferably include at least one selected from the group consisting of an amplifier (e.g. op amp) and a filter.

In another embodiment of the invention, the at least one probe comprises a plurality of probes, the plurality of probes disposed in solution. This system can further include a microfluidic system having a plurality of microfluidic channels, the microfluidic system for directing samples through the microfluidic channels to the plurality of probes. The microfluidic system can comprise a capillary electrophoresis array, a liquid chromatography array, a gas chromatography array and a lab-on-a-chip system.

The system can include structure for application of energy sufficient to kill selected cells in a location proximate to any of the plurality of probes following detection of the target within a body. The selected cells comprise cancer cells.

The system can utilize the "multiplex" SERS molecular probe(s) to allow diagnostics of multiple targets simultaneously. In this embodiment the at least one pin loop can comprises a plurality of pin loops bound to the nanoparticle, the plurality of pin loops providing at least two different loop sequences for simultaneously detecting a plurality of target sequences.

A method of detecting targets comprises the steps of introducing at least one oligonucleotide-based surface-enhanced Raman spectroscopy molecular probe (SMP) as described above to human or animal cells. The SMP is irradiated. It is then determined if the target sequence is present in the body based on analysis of SERS radiation scattered by the SMP responsive to the irradiating step. The method can include the step of lysing the cells prior to the introducing step, wherein the method is performed in-vitro. Alternatively, the SMP can be introduced into the body of the person or said animal, wherein said method is performed in-vivo. In this embodiment, the SMP can be injected into the body, such as by driving the SMP inside at least a portion of the cells.

The detection of the target sequence can indicate the presence of an abnormal gene sequence. The abnormal gene sequence can comprise cancer. When the determining step indicates the presence and position of an abnormal gene, the method can include the step of delivering energy to said position sufficient to kill at least some cells proximate to the position. The energy applied can comprise IR radiation from 700 to 900 nm. The nanoparticles can absorb the applied energy and provide heat to the surrounding cells thus allowing remote irradiation to affect the surrounding tissue/cells for site-specific and disease-specific therapy.

By using the multiplex SMP described above, the determining step can provide simultaneous detection for a plurality of different target sequences.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

An oligonucleotide-based SERS molecular probe (SMP) includes at least one loop sequence complementary to at least one target sequence. The loop sequence is disposed between a first stem sequence including an attached SERS active label and a second stem sequence including at least one attached nanoparticle, the nanoparticle including at least a metal component. The SMP generates a stronger SERS signal upon irradiation with excitation radiation when not bound to the target as compared to a SERS signal following hybridization of the probe with the target sequence. The SMP can comprise DNA as well as PNA sequence segments, or a combination of DNA and PNA segments.

Figure 1A:
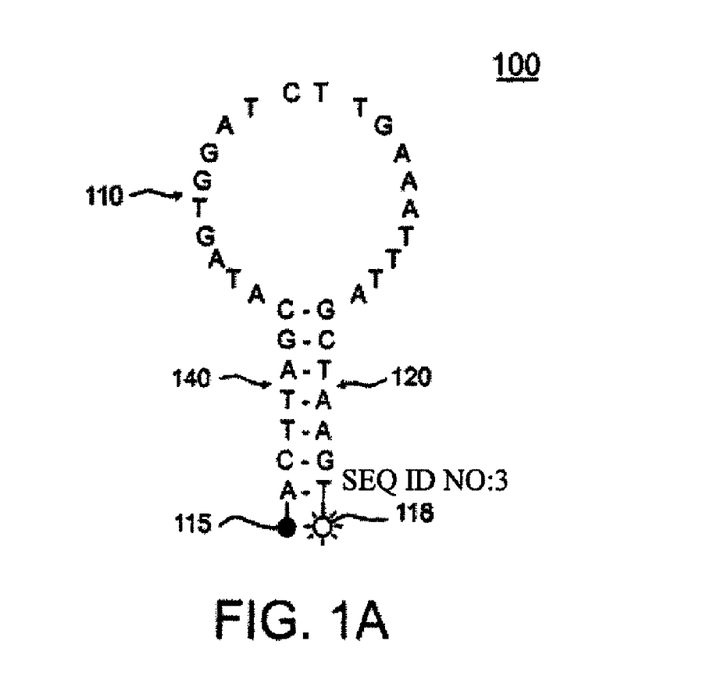
FIGS. 1(A) and (B) show a single pin loop SERS molecular probe (SMP) in the presence of no target sequence and in the presence of its intended target sequence, respectively, according to an embodiment of the invention.

FIG. 1(A) shows an exemplary single pin loop SERS molecular probe (SMP) 100 when its complementary target sequence is not present. SMP 100 includes a middle loop sequence 110 comprising an exemplary 20-base oligonucleotide sequence which is complementary to the gag gene region of the HIV1: (ATAGTGGATCTTGAAATTTA) (SEQ ID NO:1). Middle loop sequence 110 has first and second 7-nucleotide-long stem sequences 140 and 120 attached to its respective ends, CGATTCA and GCTAAGT. Typically, the middle loop sequence will include 16 to 25 bases, while the stems 140 and 120 will generally each include 5 to 8 bases. However, loop sequences and stem sequence lengths can be above or below these ranges.

The first stem region 120 includes a SERS label molecule 118 attached to its end (T) and the second stem region 140 includes at least one nanoparticle including at least a metal component 115 attached to its end (A). It is noted that although FIG. 1 shows nanoparticle 115 having a size smaller that the other components of SMP 100, this is generally not the case since nanoparticle 115 is generally on the order of a 100 nm diameter, while other components of SMP are generally on the order of several nanometers.

Nanoparticle 115 can be entirely a metal nanoparticle, or a combination of metal and non-metal components. For example, in the case of the combination metal and non-metal components, the nanoparticle 115 can comprise an electrically insulating core coated with a metallic surface. Alternatively, the nanoparticle can comprise a metallic core coated with a thin (e.g. several Angstroms to nanometers) non-metal coating, such as silica, a polymer, protein, antibody or a plurality of other bioreceptors. The combination metal and non-metal nanoparticles can have continuous (encapsulating) or non-continuous coating layers.

Although label 118 and nanoparticle 115 are shown attached to the end of their respective stem regions, label 118 and nanoparticle 115 are in no way limited to this arrangement. However, end attachment of label 118 and nanoparticle 115 is generally preferred to provide maximum separation when the loop is open (See FIG. 1(B)).

When the complementary target sequence is not present, the two stem regions 140 and 120 remain hybridized as shown in FIG. 1(A) to each other since they have complementary sequences, thus forcing stemmed loop probe 100 to have SERS label 118 and nanoparticle 115 in close physical proximity. For example, the 5'-end of the end of the sugar from the nucleotide with base T on the end of stem 120 can be bound to SERS label molecule 118, with the 3'-end the end of the sugar from nucleotide with base A on the end of stem 140 bound to nanoparticle 115. This results in a strong SERS signal through the SERS effect of SERS label molecule 118 together with nanoparticle 115 when irradiated.

Figure 1B:
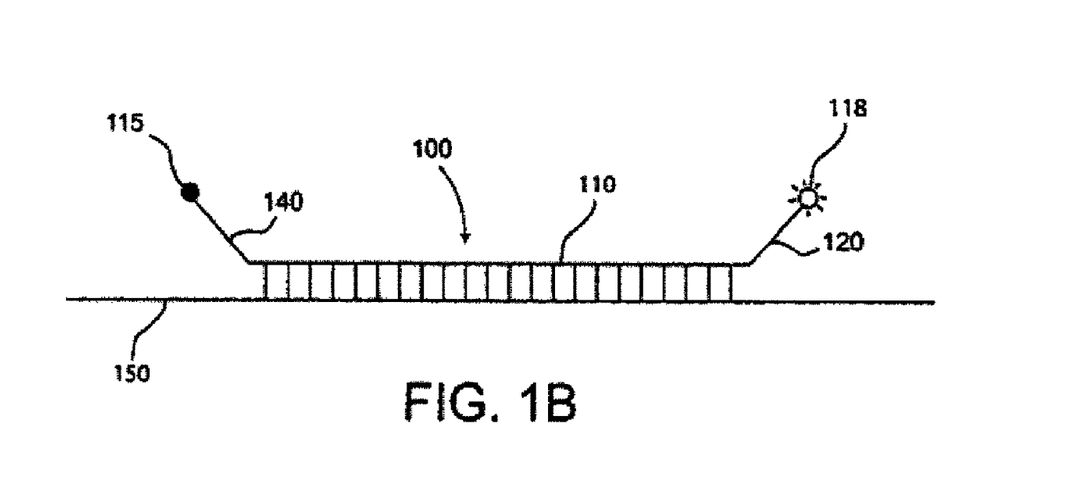

However, as shown in FIG. 1(B), when the target DNA or other sequence 150 is present, the middle loop sequence 110 opens up due to hybridization with the target sequence 150 as shown in FIG. 1(B), thus moving the stem 120 and associated SERS label 118 and stem 140 and associated nanoparticle 115 further apart. In the open configuration shown in FIG. 1(B), SMP 100 produces either no Raman signal or a substantially reduced Raman signal upon irradiation.

SMPs 100 generally include one or more SERS labels or tags attached thereto. In general, SMP 100 includes tags or labels but the target does not. However, although not generally preferred, the target can include a label, or both the target and SMP 100 can each include labels. Examples of SERS labels that can generally be used with SMP 100 include cresyl fast violet (CFV), cresyl blue violet, brilliant cresyl blue (BCB), rhodamine-6G, para-aminobenzoic acid, erythrosin, and aminoacridine.

The SMP 100 operating principle is based on the enhancement mechanisms of the SERS effect induced between the SERS-active label 118 and the metal comprising nanoparticle 115. There are two main sources of electromagnetic enhancement for the SMP 100. First, the excitation source (e.g. laser) generated electromagnetic field is enhanced due to the addition of a field caused by the polarization of the metal comprising nanoparticle 115. Second, in addition to the enhancement of the excitation laser field, there is also another enhancement due to the label molecule 118 radiating an amplified Raman field, which further polarizes the metal comprising nanoparticle 115, thereby acting as an antenna to further amplify the Raman signal.

A major contribution to electromagnetic enhancement is due to surface plasmons. Surface plasmons are associated with collective excitations of surface conduction electrons in metal comprising nanoparticles 115. Raman enhancements result from excitation of these surface plasmons by the incident radiation. At the plasmon frequency, the metal comprising nanoparticle 115 becomes highly polarizable, resulting in large field-induced polarizations and thus large local fields on its surface. These local fields increase the Raman emission intensity, which is proportional to the square of the applied field at the molecule. Additional enhancement is due to excitation of surface plasmons by the Raman emission radiation of the molecule. Electromagnetic enhancement mechanisms are characterized by the dipole fields induced in polarizable metal particles varying as the inverse cube of the distance to the center of the particle. Due to this feature, the SERS effect decrease rapidly when the distance between the SERS label 118 and the metal comprising nanoparticle 115 increases.

The binding of SERS active labels such as Rhodamine-B to SMP 100 can be performed using well established procedures [L. Allain and T. Vo-Dinh, "Surface-Enhanced Raman Scattering (SERS) Detection of a Breast Cancer Susceptibility Gene (BRCA1) Using Microarrays of Silver-Based Substrates", Anal. Chim Acta, 2001]. For example, Rhodamine-B can be coupled to amino-labeled DNA, after the formation of a labile succinimidyl ester intermediate in MeCN. To avoid hydrolysis competition, the DNA is dissolved in MeOH with 8% $H_2O$. In a sterile vial, 2.38 mg of Rhodamine B (4.97 $\mu_m$M) and 2.40 mg of O—(N-succinimidyl)-N,N,N',N'-tetramethyluronium tetrafluoroborate (9.30 $\mu_m$mol) are then dissolved in 300 $\mu_m$L of MeCN. To this solution, 5.0 $\mu_m$L of diisopropylethylamine (29 $\mu_m$mol) is added, vortexed, and allowed to react overnight. A stock solution of a 5'-amino labeled oligonucleotide is prepared by dissolving 3.69 mg (0.520 $\mu_m$mol) in 90 $\mu_m$L H2O and 950 $\mu_m$L MeOH. From this stock solution, 100 $\mu_m$L is transferred to the Rhodamine-succinimidyl ester solution in MeCN, and vortexed. After one day, the vial is refrigerated to −20 C, and 90 $\mu_m$L of 3 M sodium acetate is added, along with 200 $\mu_m$L of isopropanol (iPrOH) to force DNA precipitation. The solution is lyophilized to a final volume of about 100 $\mu_m$L, after which 400 $\mu_m$L of EtOH and 100 $\mu_m$L of iPrOH are added. The vial is then kept at −20 C overnight. A large amount of precipitate is observed. The system is centrifuged and the precipitate is washed with EtOH. This washing step is repeated five times, after which no free Rhodamine-B is observed in the ethanolic wash solution. The solid is lyophilized, redissolved in 200 $\mu_m$L of $H_2O$, and kept at −20 C.

Binding metallic surfaces such as silver nanoparticles to SMP 100 can also be performed using established procedures [L. Allain and T. Vo-Dinh, "Surface-Enhanced Raman Scattering (SERS) Detection of a Breast Cancer Susceptibility Gene (BRCA1) Using Microarrays of Silver-Based Substrates", Anal. Chim. Acta, 2001]. For example, silver nanoparticles or nanoparticles freshly coated with silver are kept under vacuum prior to use. EtOH is degassed with $N_2$ for 40 min. The Ag particles are immersed in 100 mL of an ethanolic solution containing 0.4 $\mu_m$M of 1-mercaptoundecanoic acid and 4.0 $\mu_m$M of 1-mercaptoundecanol for 30 min. The silver surfaces are washed with the degassed EtOH and air-dried. A solution containing 15.3 mg of O—(N-succinimidyl)-N,N, N',N'-tetramethyluronium tetrafluoroborate (50.8 $\mu_m$mol), 50 $\mu_m$L of diisopropylethylamine (287 $\mu_m$mol), and 1000 $\mu_m$L of MeCN is distributed over the clean Ag surfaces of the nanoparticles, and kept in an air-tight container for 15 h. The chemically treated silver surfaces are subsequently washed with MeCN (7 portions of 3 mL) and air-dried. These substrates are then transferred to a Petri dish vapor-saturated with 8% $H_2O$ in MeOH. A stock solution of the 5'-amino-labeled capture-probe sequence is prepared by dissolving 3.27 mg (0.457 $\mu_m$mol) in 90 $\mu_m$L $H_2O$ and 950 $\mu_m$L MeOH. Aliquots (15 $\mu_m$L) of this stock solution are applied to the substrates (except for the blank), and immediately exposed to broadband UV radiation for 60 s. The silver substrates are rehydrated with 8% $H_2O$/MeOH, covered with a microscope cover slide, and kept in an airtight container for 6 h.

Metal comprising nanoparticles can also be prepared and bound to biomolecules (e.g. DNA) by a variety of other known methods. For example, nanoparticles of metal colloid hydrosols can be generally prepared by rapidly mixing a solution of $AgNO_3$ with ice-cold $NaBH_4$. The immobilization of biomolecules, such as DNA, antibodies and enzymes to a solid support through covalent bonds usually takes advantage of reactive groups such as amine ($-NH_2$) or sulfide ($-SH$) that naturally are present or can be incorporated into the biomolecule structure. Amines can react with carboxylic acid or ester moieties in high yield to form stable amide bonds. Thiols (S—Au) can participate in maleimide coupling yielding stable dialkylsulfides.

In the present invention, silver nanoparticles have generally been used. The majority of immobilization schemes involving Ag surfaces utilize a prior derivatization of the surface with alkylthiols, forming stable linkages. Alkylthiols readily form self-assembled monolayers (SAM) onto silver surfaces in micro molar concentrations. The terminus of the alkylthiol chain can be directly used to bind biomolecules, or can be easily modified to do so. The length of the alkylthiol chain was found to be an important parameter, keeping the biomolecules away from the surface. Furthermore, to avoid direct, non-specific DNA adsorption onto the surface, alkylthiols can be used to block further access to the surface, allowing only covalent immobilization through the linker.

Silver surfaces have been found to exhibit controlled self-assembly kinetics when exposed to dilute ethanolic solutions of alkylthiols. The tilt angle formed between the surface and the hydrocarbon tail generally ranges from 0 to 15°. There is also a larger thiol packing density on silver, when compared to gold.

After SAM formation on silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield.

SMP 100 has a similar "hairpin" appearance to molecular beacon probes first disclosed by Tyagi which were described in the background of this application. Both molecular beacons and SMP 100 include a loop sequence disposed between two stem sequences. However, the respective probes have several significant structural and functional differences. First, Tyagi's molecular beacons operate via fluorescence and include a fluorescent label on the end of a first stem while SMP 100 operate via SERS and includes a SERS label on the end of a first stem. SERS and fluorescent labels are generally distinct species, although in some cases a fluorescent labels can also provide Raman and SERs signals.

Second, molecular beacons include a quencher molecule on the end of the second stem to quench the fluorescence from the fluorophore on the first stem, while the SMP 100 includes a metal nanoparticle on the end of stem opposite the label containing stem to enhance the Raman signal. In addition, molecular beacons provide a higher relative signal level in the presence in the target sequence as compared to no target, while the SMP 100 provides a higher signal level when no target sequence is present.

Diagnostics using SMP 100 are also superior to the fluorescence molecular beacon technique because Raman spectroscopy provides a much better multiplex advantage. For example, 100 Raman labels may be used with SMP according to the invention instead of 3-4 labels in fluorescence. Improved multiplex capability of Raman/SMP over fluorescence results because individual fluorescent lines are generally 50 to 200 nm wide at room temperature, while a SERS assay using SMP 100 results in a line width which is substantially less than 1 nm. The Raman/SERS line width is defined by the laser line width which is generally much less than 1 angstrom and the spectral resolution of the spectrometer or detector system which can have a comparable spectral resolution.

Figure 2A:
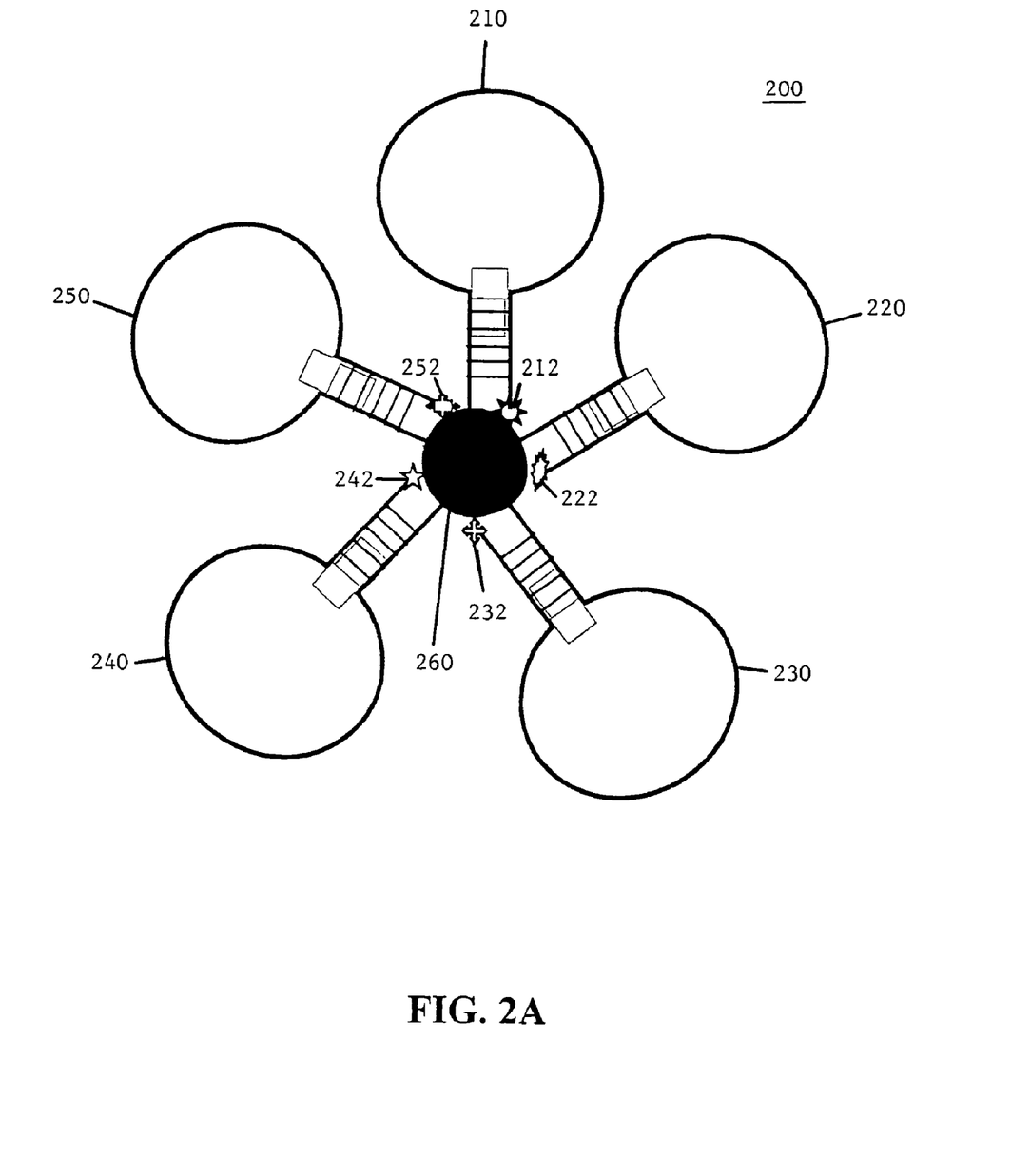
FIG. 2(A) shows a multiplex SERS molecular probe (SMP) having a plurality of different pin loops each having different labels, according to an alternate embodiment of the invention.

Another feature of the invention is a SMP adapted for simultaneous multiplexed detection of a plurality of different target sequences. FIG. 2(A) shows a multiplex SERS molecular probe (SMP) 200 having a plurality of different pin loops 210, 220, 230, 240 and 250 all attached to a single metal comprising nanoparticle 260 when none of their respective target sequences are present, according to an alternate embodiment of the invention.

A single nanoparticle 260 can support a very large number of SMPs. For example, assuming the nanoparticle 260 which typically has a radius from about 10 nm to 100 nm has a radius (R) of 30 nm, the surface area (S) of nanoparticle 260 is:

$$S=4\pi R^2=4\times 3.4\times 30^2=4\times 3.4\times 900=12,240 \text{ nm}^2$$

The foot print of the SMP is defined by the distance (d) between the DNA strands of the hybridized part, typically being 2 nm to 2.5 nm. Using d=2.5 nm, r=1.25 nm, and the associated footprint (circular area) is:

$$s=\pi r^2=4.5 \text{ nm}^2$$

Thus, the number of possible SMPs on a nanoparticle 260 having a radius=30 nm is:

$$N=S/s=2,720.$$

Even taking into account the steric hindrance of the pin loop, estimated to be a factor 10 less), a single nanoparticle 260 having a radius of 30 nm can support about 270 SMPs.

Each pin loop has a different SERS label having different and distinguishable emission spectra. Loop 210 includes label 212, loop 220 includes label 222, loop 230 includes label 232, loop 240 includes label 242 and loop 250 includes label 252. Although not shown in FIG. 2(A), pin loops 210, 220, 230, 240 and 250 each open independently when their target DNA is present. Thus, SMP 200 can be used to simultaneously detect the presence of any combination of five (5) different target sequences when irradiated. Although SMP 200 includes five (5) loops, this embodiment of the invention can include more or less than five (5) loops.

Figure 2B:
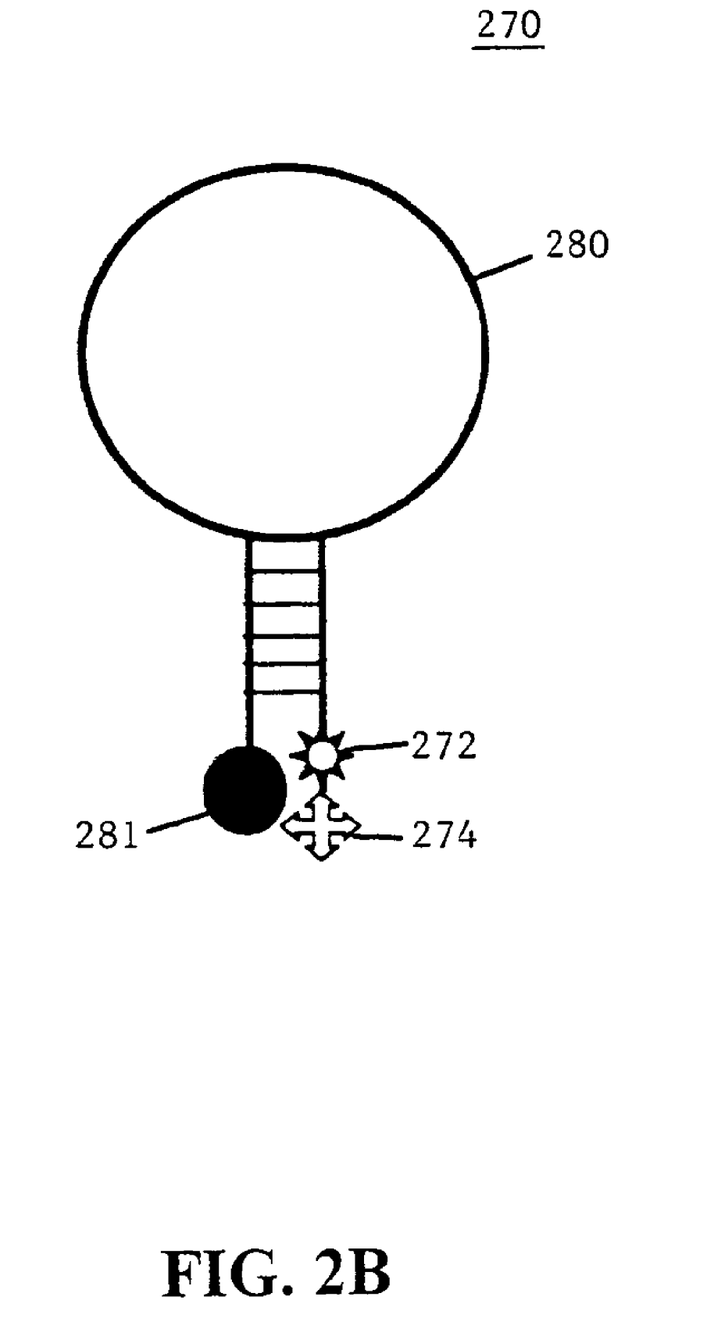
FIG. 2(B) shows a single pin loop SMP having two different labels, according to an embodiment of the invention.

FIG. 2(B) shows a single pin loop SERS molecular probe (SMP) 270 having loop 280, metal comprising nanoparticle 281 two different SERS labels 272 and 274. Label 274 is bound to label 272, while label 272 is attached to the end of one of the stem portions of SMP 270. By using a combination multiple labels, the number of distinguishable SMP types can be extended, such as each specific for a target.

Figure 3:
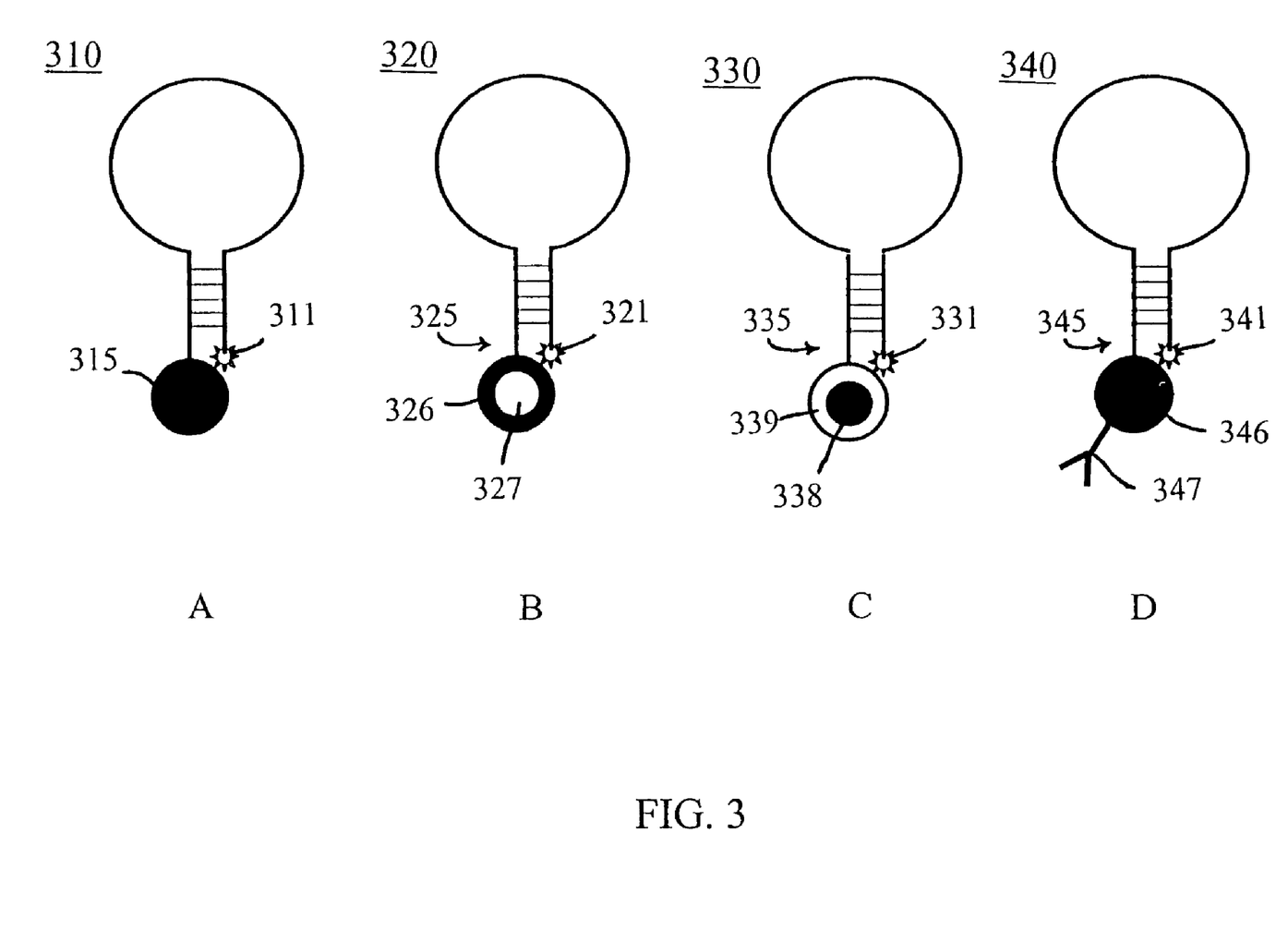
FIGS. 3(A)-(D) each show different SMP probe designs, according to another embodiment of the invention.

FIGS. 3(A)-(D) each show different SMP probe designs based on different nanoparticle arrangements, according to another embodiment of the invention. FIG. 3(A) shows an SMP 310 including a metallic nanoparticle 315 and label 311. This configuration is analogous to SMP 100 shown in FIG. 1(A). FIG. 3(B) shows SMP 320 which comprises nanoparticle 325 and label 321, nanoparticle 325 including a metal nanoshell 326 on a non-metal core 327. FIG. 3(C) shows SMP 330 which comprises nanoparticle 335 and label 331, nanoparticle 335 including metal core 338 surrounded by non-metal shell 339.

FIG. 3(D) shows SMP 340 which comprises nanoparticle 345 and label 341, nanoparticle 345 including a metal nanoparticle 346 with a bioreceptor 347 bound thereto. Bioreceptor 347 can comprise antibody, a protein, a biomimetic, an enzyme, a cell receptor intact biological cell or other bioreceptor. The bioreceptor adds functionality to SMP 340 and allows it to be targeted to specific biotargets. For example an antibody targeted against a specific cell receptor or tumor cells allow targeting the SMP to these specific biotargets. This provide a "dual-functionality" to the SMP probe. The bioreceptor 347 is for targeting and label 341/nanoparticle 346 is for diagnostics/detection.

Figure 4:
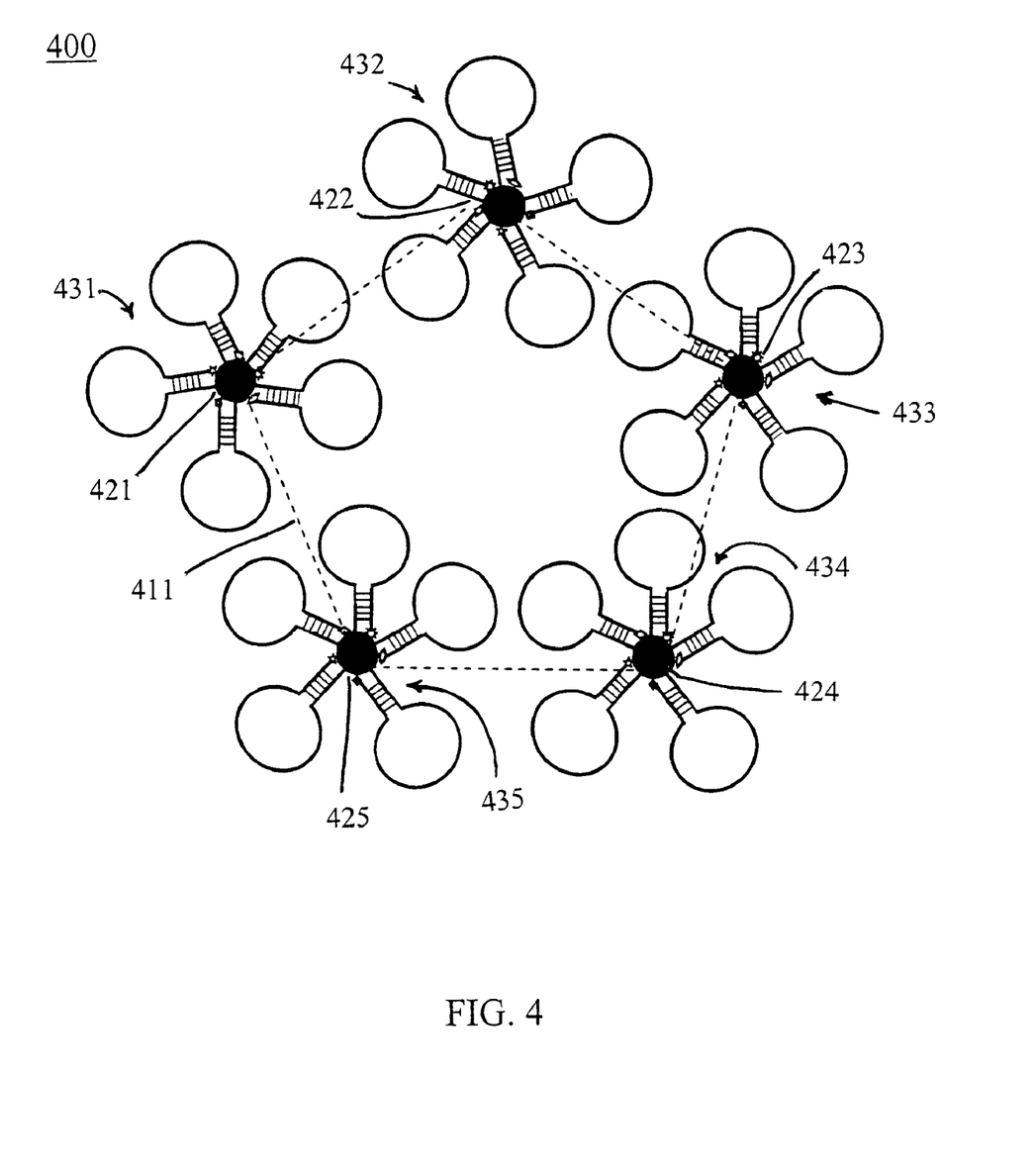
FIG. 4 shows a multi-nanoparticle interconnected SMP network, according to yet another embodiment of the invention.

FIG. 4 shows a multi-nanoparticle SMP network 400, according to yet another embodiment of the invention. SMP network 400 shown in FIG. 4 includes five metal nanoparticles 421-425 which are bound together using linker 411. Each nanoparticle 421-425 is a component of a multiplex SERS molecular probe (SMP) 431-435, each SMP 431-435 having a plurality of different pin loops each having different labels, such as the SMP 200 shown in FIG. 2A. Linker 411 can comprise DNA strands or other types of chemical bonds, such as thiol bonding. Thiol bonding is generally the best linker between metal nanoparticles, preferably using alkanedithiols [$HS(CH_2)nSH$, n=5, 6, 8, 9, 10 . . . ]. For more information on linkage through alkanedithiols, see for example "Silver Ions Adsorbed to Self-assembled Monolayers of Alkanedithols on Gold Surfaces Form Ag-dithiol-Au Multilayer Structures" by Deng et al., Appl. Phys. A 71, 639-642 (2000).

In a typical assay using the invention a plurality of SMP 100 immobilized on a solid surface and are exposed to a sample which may contain the target analyte. The probe is then irradiated. It is then determined whether the target analyte is present in the sample from analysis of SERS radiation scattered by SMP 100 responsive to the irradiating step, a low or non-measurable SERS signal corresponding to the presence of the target.

The invention can be used for a broad range of applications. For example, for development of low-cost diagnostic biochips for medical diagnostics medical therapies, environmental monitoring, high-throughput drug screening, and homeland defense applications.

The detection can be placed remotely from the SMP-based system or placed close to the SMP based system. In one embodiment the detection system is communicably connected to the SMP 100. The detector can be a photomultiplier, a phototransistor, a photodiode, a photodiode or phototransistor array, a charge-coupled device (CCD), a charge-injection device (CID) or other suitable photometric detection system. In one embodiment, the detection system part of an integrated circuit based "biochip" detection system capable of receiving and processing an optical signals emanating from SMP 100.

In a preferred biochip embodiment, the invention uses either an integrated phototransistor detector array or integrated photodiode detector array based detection system. For example, the biochips can include a large-area, n-well integrated amplifier-photodiode array designed as a single, custom integrated circuit (IC), fabricated for the biochip. For example, photodiode detector array based detection systems having 100 channels (10×10 array) have been built to support multi-channel biochip-based systems.

The IC detector is optically coupled to a multi-array sampling platform which includes receptor probes and is designed for monitoring very low light levels, such as $10^{-12}$ amperes, or less. Individual photodiodes have been fabricated having a 900-µm square size arrayed on a 1-mm spacing grid. These photodiodes and the accompanying electronic circuitry have been fabricated using a standard 1.2-micron n-well CMOS process, although, current embodiments can make use of reduced feature size processes, such as 0.10 µm processes, or below. The use of this type of standard process allows the production of photodiodes and phototransistors as well as other numerous types of analog (e.g. filters and amplifiers) and digital circuitry (e.g. digital signal processors) on a single IC chip.

This feature is the main advantage of the CMOS technology in comparison to other detector technologies such as charge-coupled devices (CCD) or charge-injection devices. The photodiodes themselves are produced using the n-well structure that is generally used to make resistors or as the body material for transistors. Since the anode of the diode is the p-type substrate material, which is common to every circuit on the IC chip, only the cathode is available for monitoring the photocurrent and the photodiode is constrained to operate with a reverse bias.

SMPs 100 can be bound to a solid sampling platform of a SERS biochip, such as integrated into biochip-based systems. For example, SMP 100 can be applied to SERS biochip systems disclosed in copending U.S. application Ser. No. 10/229, 600 entitled SERS DIAGNOSTIC PLATFORMS, METHODS AND SYSTEMS INCLUDING MICROARRAYS, BIOSENSORS AND BIOCHIPS by the same inventor as the present application. Application Ser. No. 10/229,600 is hereby incorporated by reference in its entirety into the present application. However, since SMP 100 includes metal comprising nanoparticle 115, the solid sampling platform upon which SMP 100 are attached do not require the SERS active surface upon which receptors are attached as disclosed in application Ser. No. 10/229,600.

Besides being adaptable for immobilization on a solid surface as noted above, SMP 100 can be used for the detection of nucleic acids in solution obtained directly from environmental samples by simple extraction protocols or after amplification by PCR. It may also be possible to detect nucleic acids in intact cells based on the non-Raman based work of Schofield et al. [Schofield et al (Schofield, P., Pell, A. N., Kranse, D. O., Appl. and Env. Microb., 63, 1143, 1997)].

For solution applications, SMPs can also be disposed within microwells which are part of biochips. In this embodiment, SMP 100 can be contained in a microcavity wells of a biochip and preferably interfaced with a microfluidics system, thus allowing homogeneous assays analogous to systems shown in FIGS. 15A and B (single chamber microfluidics) and FIGS. 16A and B (multiple independent chamber microfluidics) in U.S. patent application Ser. No. 10/229,600.

Figure 5:
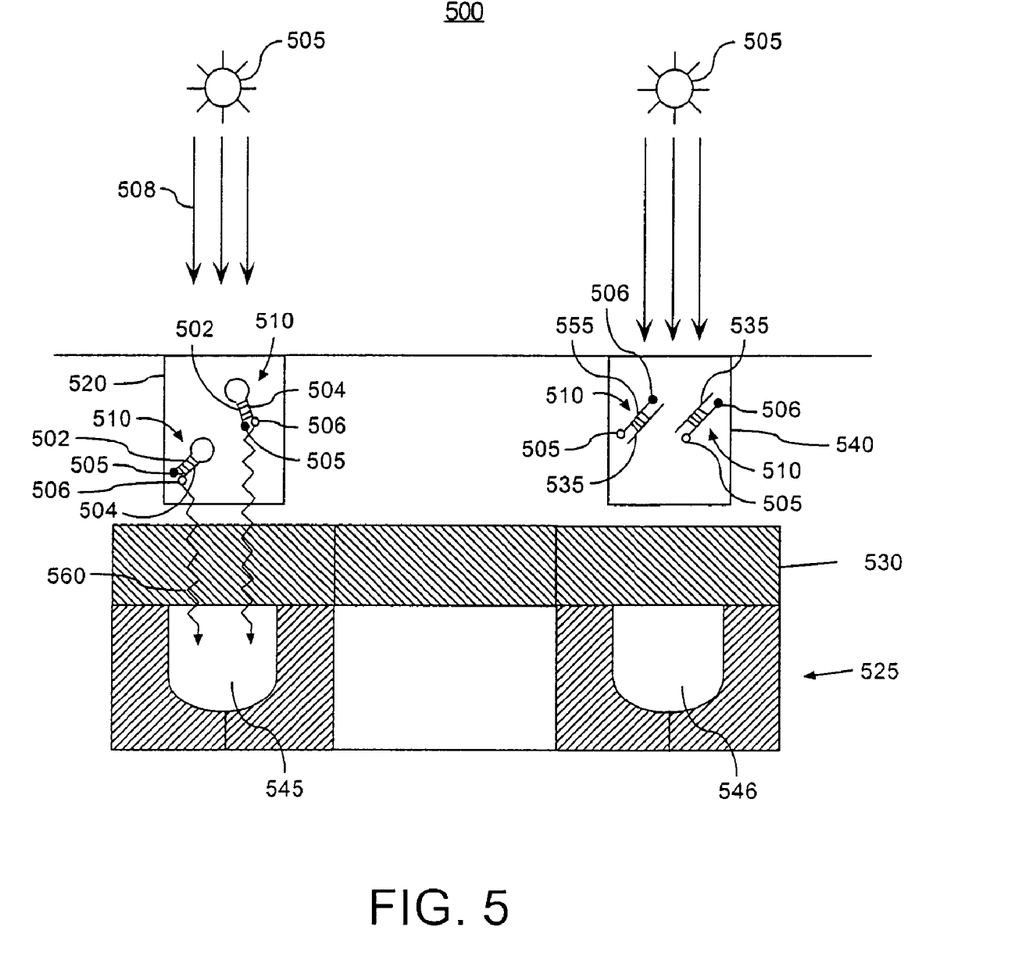
FIG. 5 shows a biochip including a first and second microwell, where in the first microwell the target for the SMPs therein is not present, while the target for the SMPs in the second well is present, according to an embodiment of the invention.

FIG. 5 shows a 2-well portion of a biochip system 500. System 500 includes excitation light source 505, such as a laser, and a plurality of microwells, including microwells 520 and 540. A microfluidics system is not shown for simplicity.

Microchip 525 includes a plurality of photodetectors 545 and 546, such as photodiodes, which convert an optical Raman signal into an electrical signal. Optical filter layer 530 is preferably disposed between the microwells 520 and 540 and microchip 525 to filter light from light source 505 and pass the Raman signal 560 from SMP 510 to photodetectors 545 and 546. SMPs 510 include SERS label 505 and metal comprising nanoparticle 506.

SMPs 510 in well 520 are shown in the absence the intended target. Since the target analyte (e.g. DNA) is not present, the two stem regions of SMP 510 remain hybridized to each other since they have complementary sequences, thus transmitting a significant Raman signal 560 upon irradiation with light 508 which can be detected by detector 545.

Well 540 includes its target 535. As a result, SMPs 510 in well 540 hybridize with target 535 resulting in loss of physical proximity between SERS label 505 and metal comprising nanoparticle 506. Thus, no Raman signal 560 is detected by photodetector 546.

The SMP can also be used in vivo for diagnostics, in vivo molecular imaging and subsequent treatment of disease. Many diseases are the result of gene mutations, which could induce some change in gene expression processes. The genetic information stored in the DNA is transcribed to the messenger RNA (mRNA) using the enzyme RNA polymerase. The mRNA copy is then utilized at the second stage of protein synthesis (translation) whereby the ribosome directs the synthesis of proteins. The presence of a specific type of mRNA is an indication of expression of the related gene. For example, the molecular basis of cancer is now widely believed to involve gene mutations which lead to dysregulated cellular proliferation and decreases programmed cell death (apoptosis).

For example, mutations of the myc protein (an apoptosis-inducing protein) or the loss of p53 protein function could result in abnormal accumulation of cells, leading to oncogenesis. In general, gene expression changes are manifested by changes (an increase or decrease) in the corresponding mRNA systems in cells. Therefore, it is possible to design SMP 100 to have the middle loop region 110 to be a cDNA sequence segment complementary to the mRNA targets of interest. For example hypoxia-inducible factor 1 (HIF-1) is a transcriptional factor of genes encoding proteins involved in tumor angiogenesis. Overexpression of HIF-1, which is correlated with tumor angiogenesis and breast cancer, can be detected using SMP systems according to the invention targeted to mRNA associated with HIF-1.

Another example for SMP diagnostics involve the HER-2/neu receptor, which belongs to the epidermal growth factor receptor (EGF-R) and is directly involved in tumor survival and proliferation. Overexpression of the HER-2/neu receptor, which has been linked to increased rate of relapse and metastasis in breast cancer, can be diagnosed using SMP systems having the stem loop region designed to be a cDNA sequence complementary to the mRNA associated to HER/neu receptor. The genes and genes products noted above are just a few examples of a wide variety of genes that can be associated with diseases. Therefore, SMP-based systems according to the invention can be used to detect and image gene expression changes in the tumor microenvironments, and subsequent development of treatment for theses specific tumor microenvironments without affecting the nearby healthy cells or tissue microenvironments.

There are several methods of performing cell-based assays using SMPs. One method consist of lysing the cells and then performing the hybridization assay. Another method consists of introducing SMPs inside the cells to be monitored. There are several methods that can be used to deliver SMP inside cells.

SMPs in solution can be injected through a microinjector, either by applying pressure, or if the SMP are magnetic (e.g., with magnetic cores), by applying a magnetic field that drives the SMP into the cells. Magnetic nanoparticles can be purchased commercially and then coated with a layer of metal. If the nanoprobes are electrically charged, a voltage can be applied to drive the SMP into the cell as an ionic current. This is a technique referred to as iontophoresis.

A pressurized microjet of an inert gas (e.g., helium) medium containing an emulsion of SMPs can also be used to inject SMPs into the cell. After injection, the gas molecules can diffuse out of the cell.

The cell membrane can also be made transiently permeable to the outside solution containing SMP by disrupting the membrane structure with a brief but intense electric shock (e.g., 2000 volts per cm for 200 μsec). Membrane bound vesicles can also be loaded with SMPs and then induced to fuse with the target cells.

The invention can be used for a variety of diagnostic and therapeutic applications. SMPs can be used to detect pathogenic species such as bacteria and viruses by targeting their DNA. For example, the invention can be used to diagnose the presence of the human immunodeficiency virus (HIV), such as by identifying the HIV gag gene sequence using the invention. Infection with the human immunodeficiency virus Type 1 (HIV1) generally results in a uniformly fatal disease. Unfortunately, standard HIV serologic tests, including the enzyme-linked immunosorbent assay and the Western Blot Assay, are not useful in the diagnosis of HIV infection during early infancy because of the confounding presence of transplacentally derived maternal antibody in infants' blood. Thus, there is a need for a direct nucleic acid based test which detects the presence of HIV viral sequences.

As noted earlier, SMP 100 shown in FIG. 1(A) has a middle portion 110 having a 20-base oligonucleotide sequence complementary to the gag gene region of the HIV1: (AT-AGTGGATCTTGAAATTTA) (SEQ ID NO:1). The middle region has two 7-nucleotide-long stem sequences 120 and 140, each from each side: e.g., CGATTCA and GCTAAGT.

Under normal conditions, when the target sequence of the gag region of the HIV1, TATCACCTAGAACTTTAAAT (SEQ ID NO:2) is not present, the two stem regions of the SMP probe 120 and 140 are hybridized to each other since they have complementary sequences, thus forming a stemmed loop which brings the SERS label 118 and metal comprising nanoparticle 115 in close proximity. Therefore, upon irradiation by a radiation source such as a laser, a strong SERS signal from the SERS label can be recorded.

When target sequences containing a sequence of the gag region of the HIV1, TATCACCTAGAACTTTAAAT (SEQ ID NO: 2) is present in the sampling area, hybridization occurs between the target and middle loop sequence 110, inducing a conformation change that separates the stem sequences 120 and 140 of SMP 100. Separation of the stems of SMP 100 results in an increased separation distance between the label molecule 118 and the metal comprising nanoparticle 115. This process produces a disappearance (or substantial decrease) in the SERS signal from the label molecule 118. Such a SMP technique can be very sensitive since single-molecule detection of SERS labels such as CFV, Rhodamine-6G or Rhodamine B can be achieved.

The invention can also be used to detect other gene sequences, such as abnormal gene sequences known to be associated with human cancer cells. These abnormal gene sequences can be identified in fluids using the invention, such as in urine. For example, the biochip shown in FIG. 5 can be used for this purpose.

Figure 6:
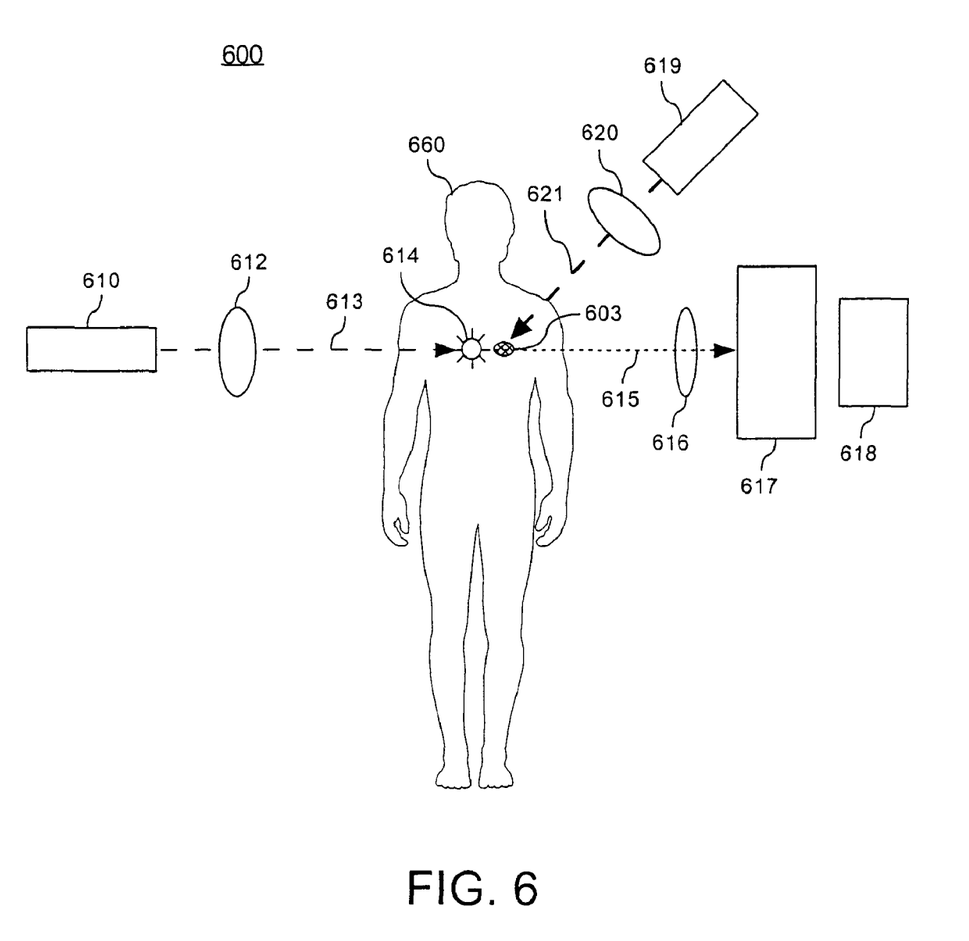
FIG. 6 illustrates a system for diagnosing the presence of tumors including cancer cells using SMPs and for applying energetic radiation to the regions in which the cancer cells are identified, according to another embodiment of the invention.

Alternatively, the invention can be used in a system 600 to identify gene sequences, including abnormal gene sequences within tissue and organs, such as those of humans as shown in FIG. 6. In this case, a solution containing SMPs targeted to a specific disease (i.e., SMP with stem loop sequence complementary to mRNA of interest) or a specific pathogen (i.e., SMP with stem loop sequence complementary to DNA of pathogens of interest) can be injected into a patient 660, such as using a syringe. The SMP 614 is transported via the blood stream to the target tissue microenvironments of interest, such as tumor 603. Alternatively, a solution of SMPs 614 can be delivered orally.

Due to their nanoscale sizes, the SMPs 614 can penetrate into cellular environments, where they interact and hybridize with the mRNA of interest. SMP molecules 614 which travel through the blood stream inside the body towards tumor 603, can be monitored using the excitation radiation 613 from laser 610, which passes through optical system 612. Upon hybridization with the mRNA target, the SMP stem loops open and the SERS signals decreases due to the increased separation distance between the SERS labels and the metal comprising nanoparticles as described previously. Due the multiplex capability of the SMP, gene expression changes (over expression, or under expression) of a large variety of genes can be detected and imaged simultaneously in vivo using a variety of different stem loop sequences each targeted to genes of interest. Due to tissue scattering and absorption properties, it is preferable to use laser excitation and subsequent Raman/SERS detection within the diagnostic window of tissue which is generally in the range from 700-900 nm (NIR). In this range, water does not significantly absorb. Although generally less preferred, the portion of the therapeutic window from 900-1200 nm may also be used.

An exemplary detection and imaging system which can be used to detect the SERS emission 615 from SMPs 614 includes a multichannel detector (e.g., CCD) 618 equipped with a dispersive device 617 (e.g., AOTF, monochromator, or optical filter) and optical filter 616. The microenvironments of the tumor 603 can be identified via interaction of SMPs 614, such as hybridization of SMP stem loops with mRMA molecules at tumor cells, as discussed previously.

Optionally, the system can also include structure for performing therapy in selected locations following detection of the target gene sequence. In the case of cancer, the therapy generally comprises application of energy in an amount and for a duration sufficient to kill the cancer cells detected. The application of energy sufficient to kill the cancer cells is preferably applied substantially contemporaneously following detection of the cancer or other condition requiring therapy by system 600.

The structure for application of energy can be selected from any of a variety of energetic sources. For example, focused ultrasound beams or laser beams may be used. Other energy sources involve focused beams of microwave or infrared radiation. The treatment procedure can be initiated using delivery of energy into the tumor site, using optional treatment components provided by system 600. One example of therapy components comprises a source of NIR radiation 619, such as an NIR laser 619 which provides NIR radiation which is directed through focusing optics 620 to patient 660.

The absorption band of metallic comprising nanoparticles provided by the SMP can be set to desired ranges to provide selective heating of the SMP, which in turn can heat its surrounding environment (e.g. tissue). As noted above, nanospheres of dielectric materials coated with a metal nanoshell have been found to be SERS active. The core diameter and the metal thickness of nanoshells can be varied to modify the SERS properties of the nanoparticles, including its absorption spectrum. The nanoparticles and nanoshells can be designed to provide enhanced electromagnetic absorption bands for a specific wavelength due to surface plasmons. [R. L. Moody, T. Vo-Dinh, and W. H. Fletcher, "Investigation of Experimental Parameters for Surface-Enhanced Raman Spectroscopy," Appl. Spectrosc., 41, 966 (1987).] Gold nanoshells surrounding a dielectric core have been developed which can be tuned to the visible and NIR spectrum. [S. R. Sershen, S. L. Westcott, N. J. Halas, and J. L. West, "Temperature-sensitive polymer-nanoshell composites for photothermally modulated drug delivery", World Biomaterials Congress 2000, May 15-20, 2000]. Therefore, the nanoparticles can be used to more efficiently absorb more electromagnetic energy and provide localized heating as compared to directly heating a desired region. This selective heating effect can be use to heat surrounding tissue for medical treatment, such as killing tumor cells as described above, or to affect cellular metabolism or growth. SMPs based on magnetic particles can also be selectively heated using an applied magnetic field.

EXAMPLES

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

Example 1

Exemplary Raman Imaging System

A Raman imaging system was tested which included a CCD mounted on a microscope device with a tunable filter such as an acousto-optic tunable filter (AOTF). This system is capable of spectral imaging cells being monitored by (SERS medical) SERMED nanoprobes. A laser such as helium-neon laser (5 mW, 632.8 nm) is used a the excitation beam. After passing through a band pass filter (Corion), the laser beam was expanded and recollimated using a spatial filter/beam expansion module, prior to entering an aperture of a microscope (e.g., Nikon, Microphot SA). Different types of microscopes (inverted, epi-luminescence, or confocal microscopes with various magnification powers) may be used depending on the application. The laser beam is collimated by a condenser lens and focused onto a sample containing cells to be monitored on the microscope viewing field.

An objective with appropriate magnification is used to focus and transmit the SERS image to the microscope image exit port equipped with a CCD used to record 2-D images. Rejection of the laser scatter was performed using a holographic notch filter (e.g., Kaiser, model HNPF-633-1.0) placed in the detection path. In the system, we also use a second (optional) exit port of the microscope to detect the SERS spectra of the sample. For the measurement of the SERS spectra, another holographic notch filter (Kaiser, model HNPF-633-1.0) is placed in the image beam, to reject the laser scatter from the SERS emission which is then focused onto an optical fiber (Fiberguide Industries). The SERS signals is transmitted via the optical fiber onto the emission slit of a spectrograph (ISA, model HR320) equipped with a thermo-electrically cooled, red-enhanced, intensified CCD (ICCD, e.g., Princeton Instruments, model RE/ICCD 5765).

If 2-D multispectral images are not required, a conventional Raman spectrometer may be used. Another system was based on a Jobin-Yvon/ISA Ramanor 2000M double-grating monochromator. The data acquisition system was an LSI 11/23 minicomputer purchased from Data Translation Corporation and a DSD/880 Winchester/floppy disk drive. Photon counting was accomplished using a cooled RCA C31034-02 photomultiplier tube. The excitation was provided by a Spectra Physics Model 171 argon ion laser. Scanning electron microscope (SEM) photographs are obtained with an ISI DS-130 scanning electron microscope. Another Raman spectrometer used was an intensified charge-coupled device (ICCD) (Princeton Instruments, model RE/ICCD) equipped with a polychromator (ISA Inc., model HR-320).

Example 2

Sensitivity of SERS for Application to SERS Biochip and SERS Molecular Probe (SMP)

Raman spectroscopy is an important analytical technique for chemical monitoring, biological analysis and medical diagnostics due to the wealth of information on molecular structures that can extracted from experimental data. The Raman cross-section, however, is inherently weak, thus preventing the possibility to achieve low detection limit with normal Raman spectroscopy. This renewed interest for Raman spectroscopy has been due to the observations of enormous Raman enhancement of the SERS effect for molecules adsorbed on special metallic surfaces. SERS detection of single molecules using silver colloid media have been reported (-Nie S., and S. R. Emory, 1997, Science, 275, 1102; -Kneipp K., Wang Y., H. Kneipp, L. T. Perelman, I. Itzkan, R. R. Dasari, M. Feld, 1997, Phys. Rev. Lett., 78, 1667). Recent improvements have been achieved towards the goal of single molecule detection of cresyl fast violet (CFV) via Raman scattering using nanostructed solid substrates including nanoparticles coated with silver (Stokes, Hueber et al, 1998; T. Vo-Dinh, Surface-Enhanced Raman Spectroscopy Using Metallic Nanostructures," Trends in Anal. Chem., 17,557 (1998)). These improvements are due to the optimization of a silver island substrate which imparts a large surface-enhanced Raman scattering (SERS) enhancement. Furthermore, a He—Ne laser enables obtaining an additional resonance enhancement factor, again raising the signal level. In the experiment performed, the detection system utilized a spectrograph equipped with a red-enhanced intensified CCD (RE-ICCD). A confocal excitation/collection geometry was implemented with a 100× objective lens. The 0.9 numerical aperture of this lens helped ensure a tight focus and efficient scattered signal collection. The SERS spectrum of CFV which was obtained from a $5 \times 10^{-11}$ M solution. A 1-uL aliquot ethanolic CFV solution (i.e., $3 \times 10^7$ molecules) was spotted on the solid SERS platform and allowed to dry after spreading to a 6.5 mm diameter. The broadness of the 595 $cm^{-1}$ band of this spectrum results from the use of a 500-μm entrance slit width to improve signal collection. Assuming a laser spot diameter of 10 μm and even distribution of CFV molecules within the 6.5-mm diameter spot, the number of probed molecules was estimated to be approximately 70.

The results showed SERS signals from fewer than 30 molecules using CFV dyes. SERS detection of single molecules using silver colloid media have been reported [Nie S., and S. R. Emory, 1997, Kneipp et al, 1997, Vo-Dinh 1998; Stokes, Hueber et al, 1998]. When these molecular probes find and hybridize to their DNA target(s), the signals of these single SMP substantially disappear, indicating the detection of single DNA targets.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

I claim:

1. A method of detecting targets, comprising the steps of:

introducing at least one oligonucleotide-based surface-enhanced Raman spectroscopy molecular probe (SMP) to a solution comprising isolated nucleic acids, said SMP comprising at least one nanoparticle having at least a metal component, and at least one pin loop, said pin loop including a loop sequence complementary to at least one target sequence, a first stem attached to one end of said pin loop having at least one SERS active label attached thereto and a second stem attached to the other end of said pin loop and said nanoparticle, wherein said probe generates a stronger SERS signal upon irradiation with excitation radiation when not bound to said target sequence as compared to a SERS signal following hybridization of said probe with said target sequence, irradiating said SMP, and determining if said target sequence is present in the solution comprising isolated nucleic acids based on analysis of SERS radiation scattered by said SMP responsive to said irradiating step.

2. The method of claim 1, wherein said pin loop includes at least one of DNA and PNA segments.

3. The method of claim 1, wherein said method is performed in-vitro.

4. The method of claim 1, wherein detection of said target sequence indicates an abnormal gene sequence.

5. The method of claim 4, wherein said abnormal gene sequence is associated with cancer cells.

6. The method of claim 1, wherein said at least one pin loop comprises a plurality of said pin loops bound to said nanoparticle, said plurality of pin loops providing at least two different of said loop sequences, said determining step providing simultaneous detection for a plurality of said target sequences.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Human immunodeficiency virus type 1

<400> SEQUENCE: 1
atagtggatc ttgaaattta                                          20

<210> SEQ ID NO 2
<211> LENGTH: 20
<212> TYPE: DNA
<213> ORGANISM: Human immunodeficiency virus type 1

<400> SEQUENCE: 2
tatcacctag aactttaaat                                          20

<210> SEQ ID NO 3
<211> LENGTH: 34
<212> TYPE: DNA
<213> ORGANISM: ARTIFICIAL
<220> FEATURE:
```

| | |
|---|---|
| <223> OTHER INFORMATION: OLIGONUCLEOTIDE | |
| <400> SEQUENCE: 3 | |
| acttagcata gtggatcttg aaatttagct aagt | 34 |